US012685825B2

(12) United States Patent
Meredith et al.

(10) Patent No.: US 12,685,825 B2
(45) Date of Patent: Jul. 21, 2026

(54) SEALED MULTI CHAMBER SYRINGE FOR STORAGE, MIXING AND DELIVERY OF MULTI PART SUBSTANCES

(71) Applicants: William R. Meredith, Raleigh, NC (US); Annette Johnson Meredith, Raleigh, NC (US)

(72) Inventors: William R. Meredith, Raleigh, NC (US); Annette Johnson Meredith, Raleigh, NC (US)

( * ) Notice: Subject to any disclaimer, the term of this patent is extended or adjusted under 35 U.S.C. 154(b) by 904 days.

(21) Appl. No.: 17/867,636

(22) Filed: Jul. 18, 2022

(65) Prior Publication Data

US 2023/0021069 A1 Jan. 19, 2023

Related U.S. Application Data

(60) Provisional application No. 63/284,034, filed on Nov. 30, 2021, provisional application No. 63/222,561, filed on Jul. 16, 2021.

(51) Int. Cl.
A61M 5/315 (2006.01)
A61M 5/28 (2006.01)

(52) U.S. Cl.
CPC ........ A61M 5/31596 (2013.01); A61M 5/284 (2013.01)

(58) Field of Classification Search
CPC .......................... A61M 5/31596; A61M 5/284
See application file for complete search history.

(56) References Cited

U.S. PATENT DOCUMENTS 3,543,967 A * 12/1970 O'Connor ............. A61M 5/284
222/386
5,665,068 A * 9/1997 Takamura ........... A61M 5/3129
604/416

* cited by examiner

*Primary Examiner* — James D Ponton
*Assistant Examiner* — John A Doubrava
(74) *Attorney, Agent, or Firm* — Kammer Browning PLLC; Mark A. Kammer

(57) ABSTRACT

A syringe device with preferred and alternate embodiments structured to store, mix (if appropriate), and dispense multiple compounds (fluids, gels, suspensions, powdered solids, etc.) without the need for multiple syringes or the repeated use of a syringe. In a first embodiment, the device stores two separate compounds for use and mixes the compounds before dispensing the combined mixture. In a second embodiment, the device stores two separate fluids for use and dispenses the first fluid followed sequentially by dispensing the second. The device may be used with a variety of dispensing structures such as an applicator or a cannula (syringe needle). The present invention finds specific application, for example, in a syringe device for storing and combining a diluent with a lyophilized drug/vaccine. Overall, the device structures a unique arrangement of chambers and channels for the accurate storage, mixing, and dispensing of multiple compounds (fluids, gels, suspensions, powdered solids, etc.).

1 Claim, 8 Drawing Sheets

1

SEALED MULTI CHAMBER SYRINGE FOR STORAGE, MIXING AND DELIVERY OF MULTI PART SUBSTANCES

CROSS REFERENCES TO RELATED APPLICATIONS

This application claims the benefit under Title 35 United States Code § 119(e) of U.S. Provisional Patent Application Ser. No. 63/222,561; Filed: Jul. 16, 2021; and U.S. Provisional Patent Application Ser. No. 63/284,034; Filed: Nov. 30, 2021; the full disclosures of which are each incorporated herein by reference.

BACKGROUND OF THE INVENTION

1. Field of the Invention

The present invention relates generally to devices for holding, combining, and dispensing fluids, especially for dispensing fluids and/or gels through a syringe. The present invention relates more specifically to a syringe device for sequentially dispensing multiple fluids and/or mixing multiple compounds (fluids, gels, suspensions, powdered solids, etc.) and dispensing the resultant mixture. The present invention finds specific application, for example, in a syringe device for storing and combining a liquid diluent with a lyophilized drug/vaccine. The device structures a unique arrangement of chambers and channels for the accurate storage, mixing, and dispensing of multiple fluids, gels, suspensions and/or powdered solids.

2. Description of the Related Art

There are a number of actions, especially in the medical field, that require sequentially dispensing multiple fluids and/or mixing and simultaneously dispensing multiple fluids. It would be beneficial to have a syringe device that could be pre-filled with the multiple fluids and configured to carry out the appropriate mixing or sequential dispensing of the fluids.

Other objectives of the present invention will become apparent to those skilled in the art upon an understanding of the structures and functions of the components and assemblies as described in detail herein below.

SUMMARY OF THE INVENTION

The present invention provides preferred and alternate embodiments of a syringe device structured to store, mix (if appropriate), and dispense multiple fluids without the need for multiple syringes, the repeated use of a syringe or separate mixing vials. In a first embodiment, the device stores a fluid (diluent for example) in one chamber and a powder (drug/vaccine for example) in the other. Upon activation, the device transfers the fluid into the chamber which holds the powder. Mixing of powder and fluid then occurs before dispensing the combined mixture. In a second embodiment, the device stores two separate fluids for use and dispenses the first fluid followed sequentially by dispensing the second. In both embodiments the devices may be used with a variety of dispensing structures such as an applicator or a cannula (syringe needle).

Other applications of the present invention will become apparent to those skilled in the art upon a consideration of the drawing figures attached and the detailed description of the preferred embodiments set forth below.

DETAILED DESCRIPTION OF THE PREFERRED EMBODIMENTS

First Preferred Embodiment

Figure 1:
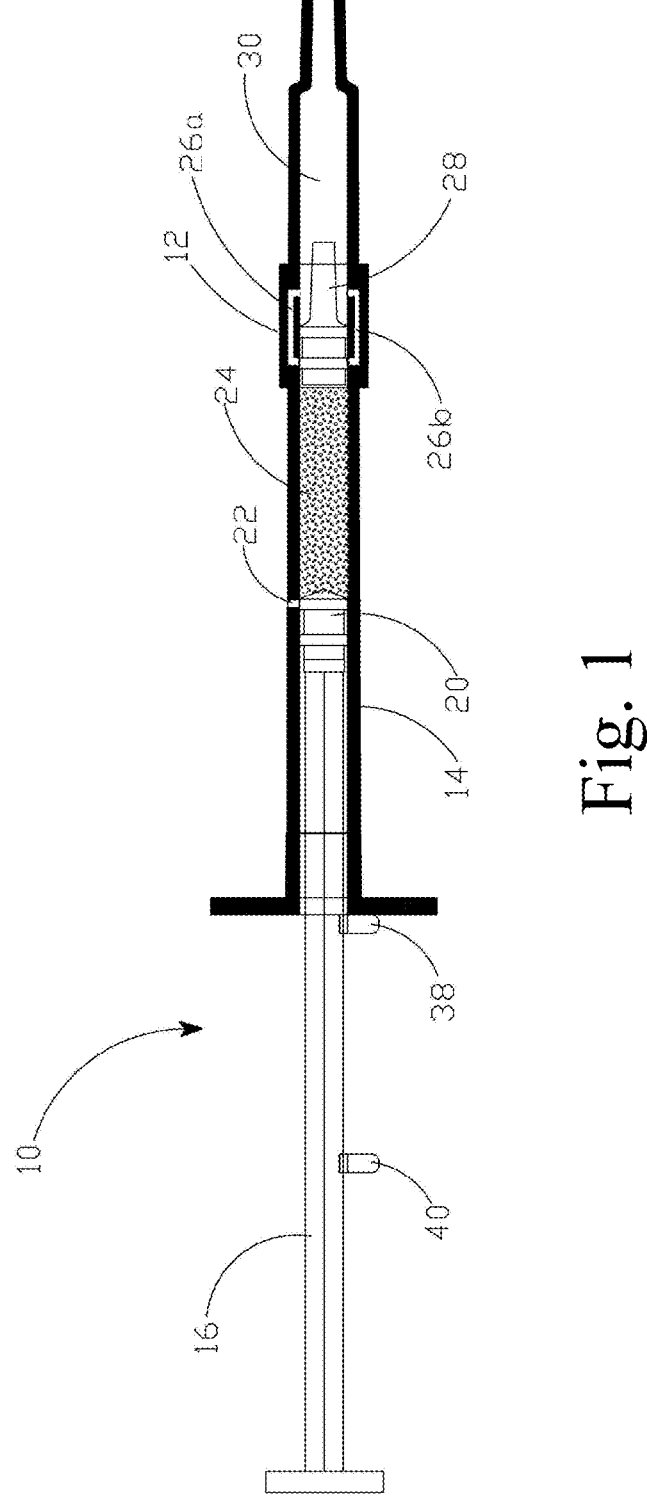
FIG. 1 is a cross-sectional view of a first preferred embodiment of the storage, mixing, and delivery device of the present invention shown in a storage condition with the plunger in its fully refracted position.

Reference is made first to FIG. 1 which is a cross-sectional view of a first preferred embodiment of the storage, mixing, and delivery device of the present invention shown in a storage condition with the plunger in its fully retracted position. The components of the first preferred embodiment, structured to mix a diluent with a lyophilized drug/vaccine (LYO) include: dual chamber syringe (LYO) 10; outer shell 12; inner syringe 14; plunger 16; diluent stopper 20; vent 22; diluent chamber 24; bypass channels 26a & 26b; injection stopper 28; mixing chamber 30; first removable tab 38; and second removable tab 40.

Figures 2A, 2B:
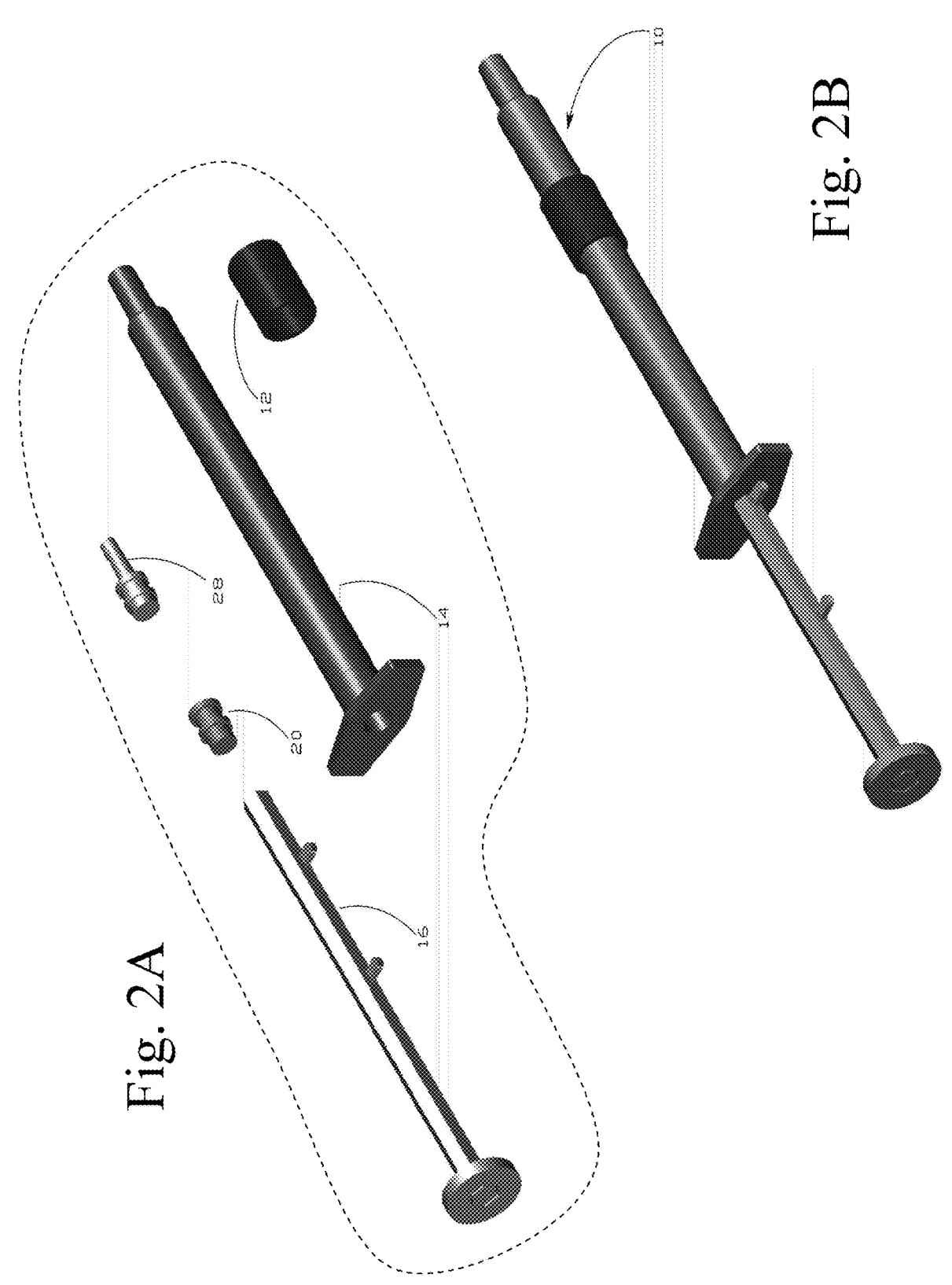
FIGS. 2A & 2B are a disassembled perspective view (FIG. 2A) and an assembled perspective view (FIG. 2B) of the first preferred embodiment of the present invention.

Reference is next made to FIGS. 2A & 2B are a disassembled perspective view (FIG. 2A) and an assembled perspective view (FIG. 2B) of the first preferred embodiment of the present invention. In these assembly views, dual chamber syringe (LYO) 10 is seen to be generally constructed of syringe outer shell 12, inner syringe 14, plunger 16, diluent stopper 20, and injection stopper 28.

Figures 3A, 3B, 3C:
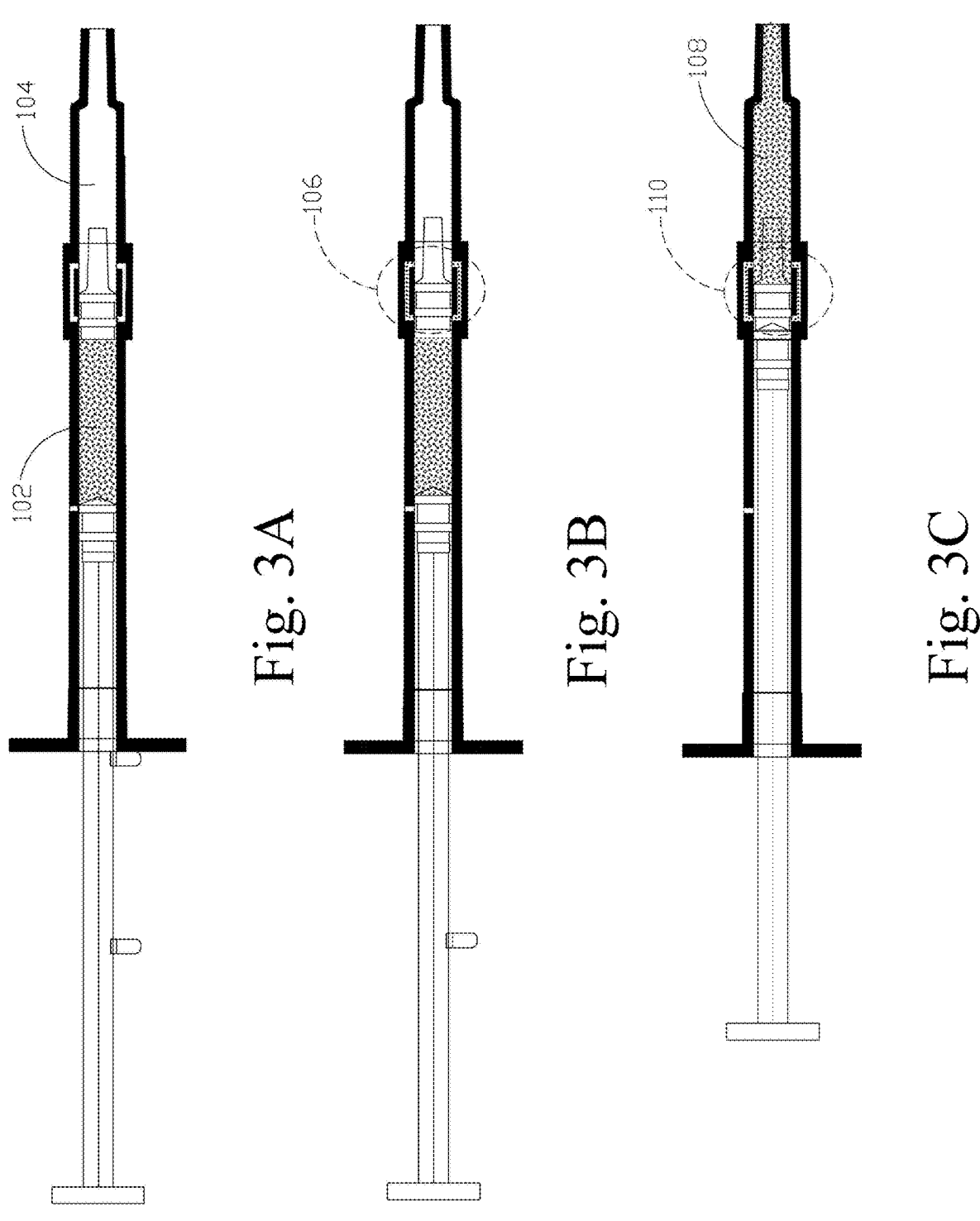
FIGS. 3A-3E are cross-sectional views of the first preferred embodiment of the storage, mixing, and delivery device of the present invention shown in progressive conditions effecting the mixing and delivery of the two-part substances.
Figures 3D, 3E:
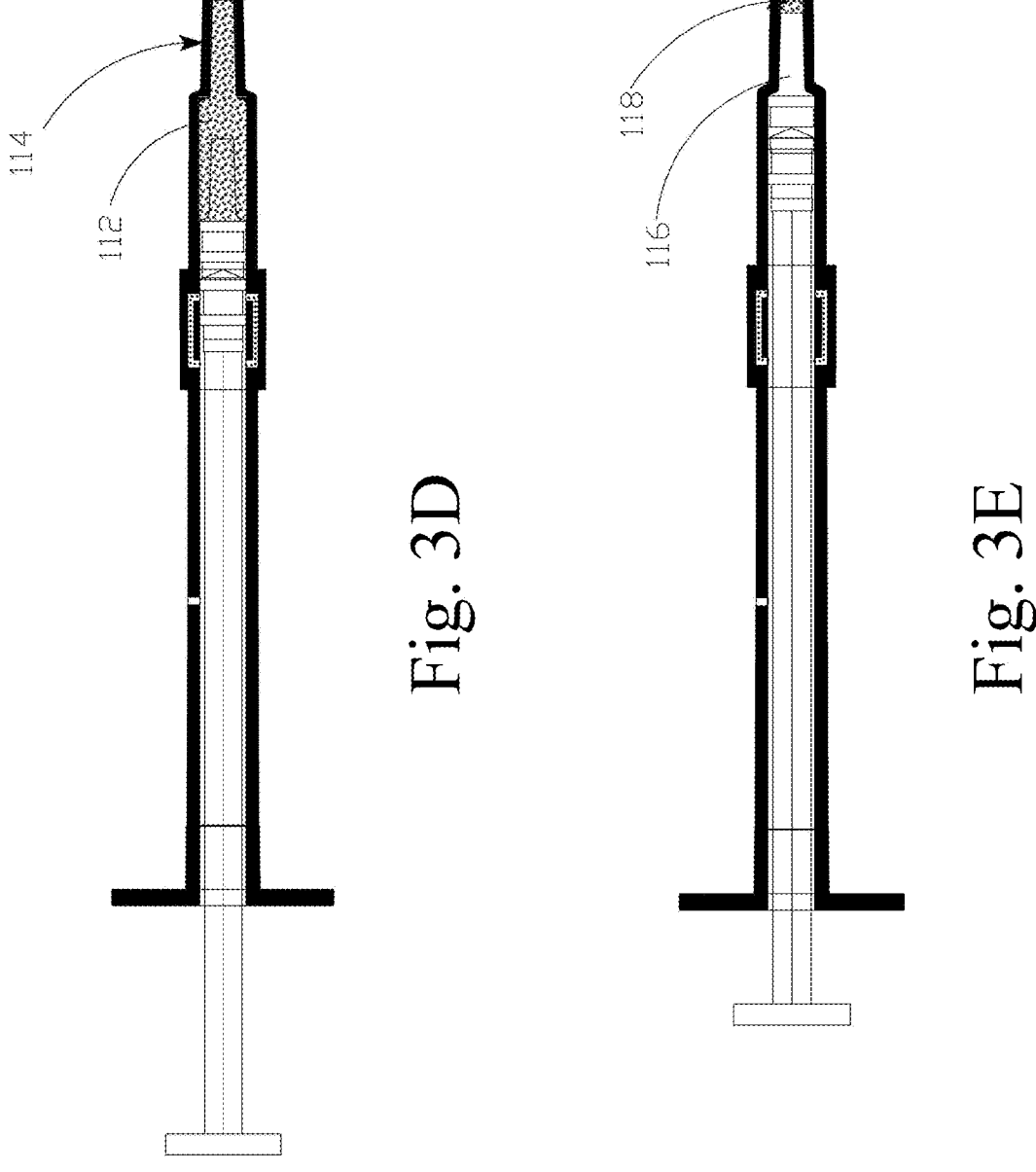

FIGS. 3A-3E are cross-sectional views of the first preferred embodiment of the storage, mixing, and delivery device of the present invention shown in progressive conditions effecting the mixing and delivery of the two-part substances. FIG. 3A shows the device in a starting position, pre-filled with diluent at position 102 and lyophilized drug/vaccine at position 104. FIG. 3B shows the first tab removed and the stoppers advanced to open the bypass channels in condition 106. FIG. 3C shows the plunger advanced to the second tab and the diluent transferred past the injection stopper at position 108. FIG. 3C also shows the lyophilized agent dissolved and the bypass channels in condition 110 closed by virtue of stopper-to-stopper contact. In this configuration, the second tab has been removed. FIG. 3D shows the stoppers advanced to initiate injection at position 112 while the bypass channels remain closed. FIG. 3D also shows the mixed two-part substance being delivered through the nozzle at position 114. FIG. 3E shows the stoppers advanced to final position 116. With the injection being complete, FIG. 3E shows the maximum solution volume forced by the long-tipped injection stopper from the nozzle at position 118.

Second Preferred Embodiment

Figure 4:
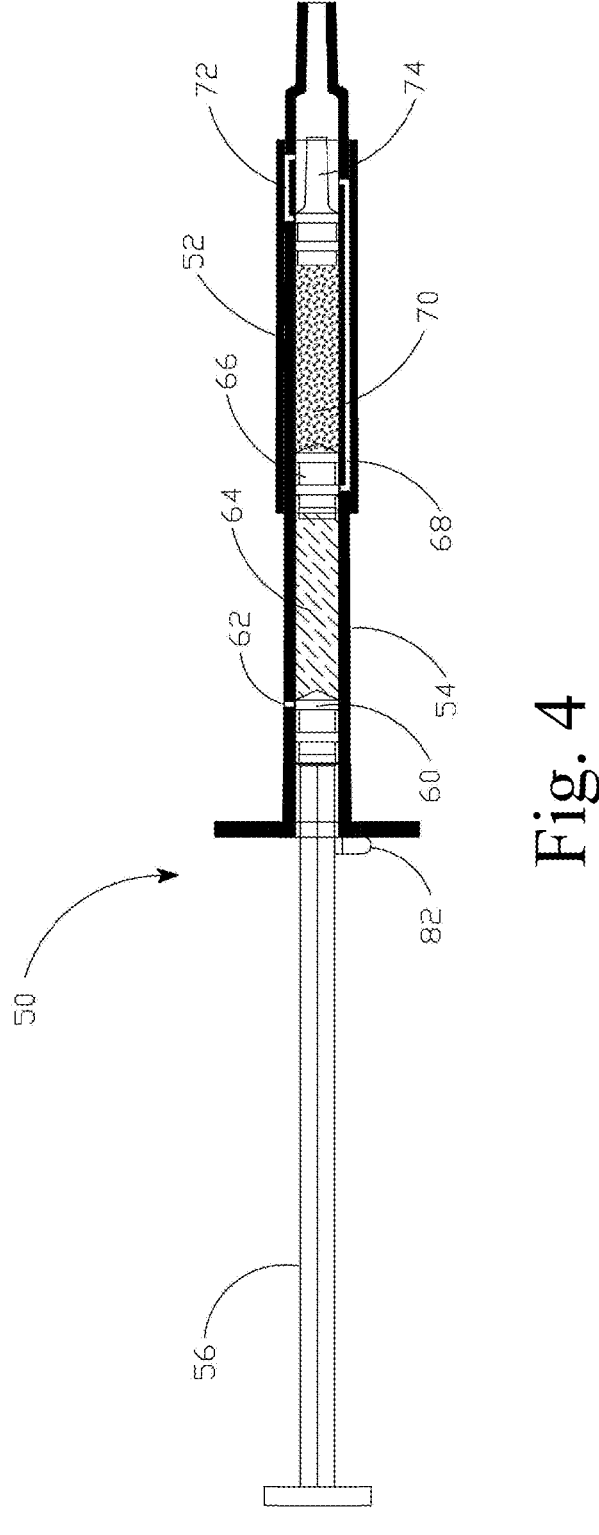
FIG. 4 is a cross-sectional view of a second preferred embodiment of the storage, mixing, and delivery device of the present invention shown in a storage condition with the plunger in its fully retracted position.

FIG. 4 is a cross-sectional view of a second preferred embodiment of the storage, mixing, and delivery device of the present invention shown in a storage condition with the plunger in its fully retracted position. The components of the second preferred embodiment, structured to sequentially dispense two separate fluids, include: dual chamber syringe (DUO) 50; outer shell 52; inner syringe 54; plunger 56; pushing stopper 60; vent 62; first liquid chamber 64; separation stopper 66; first liquid bypass channel 68; second liquid chamber 70; second liquid bypass channel 72; injection stopper 74; and removable tab 82.

Figures 5A, 5B:
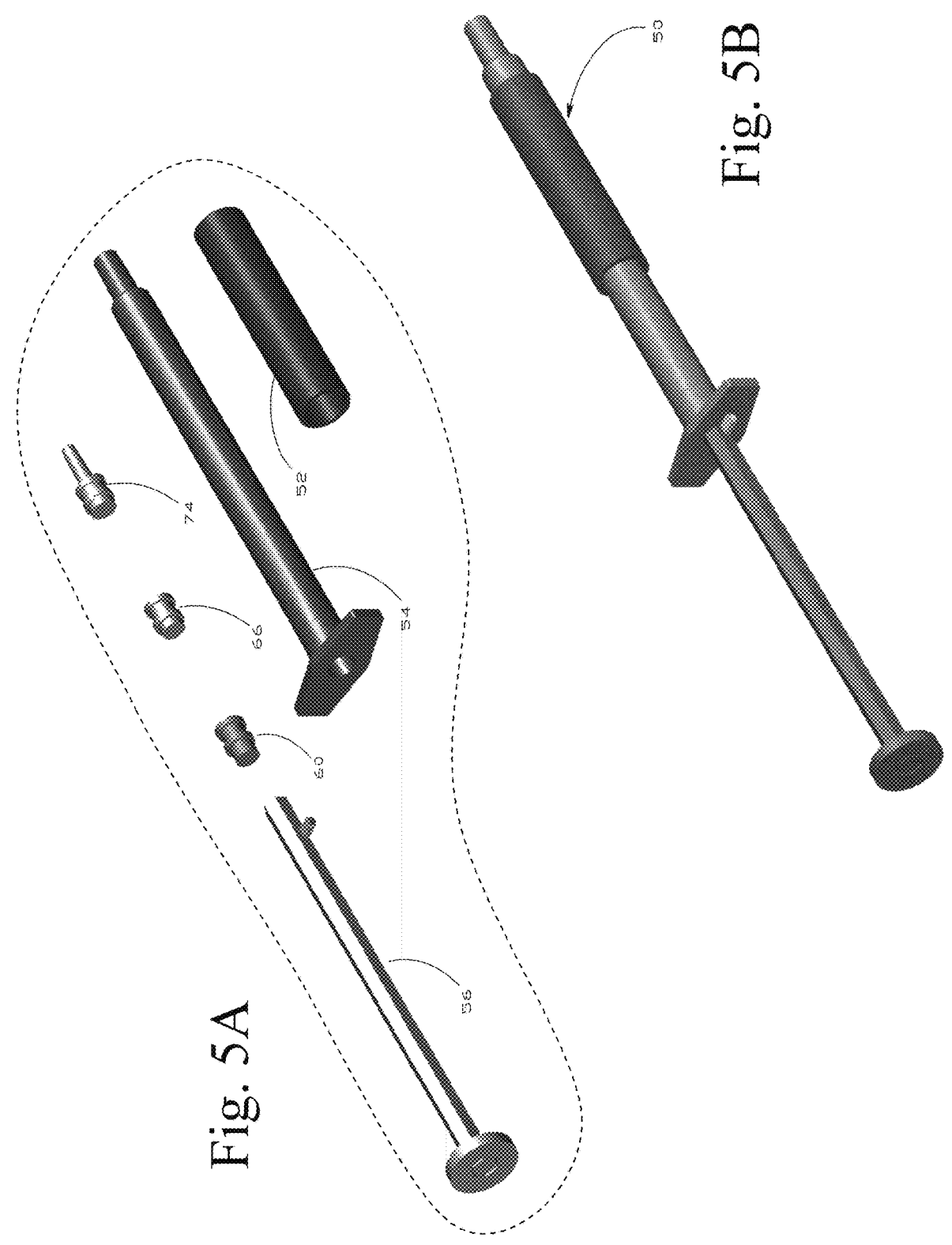
FIGS. 5A & 5B are a disassembled perspective view (FIG. 5A) and an assembled perspective view (FIG. 5B) of the second preferred embodiment of the present invention.

Reference is next made to FIGS. 5A & 5B which are a disassembled perspective view (FIG. 5A) and an assembled perspective view (FIG. 5B) of the second preferred embodiment of the present invention. In these assembly views, dual chamber syringe (DUO) 50 is seen to be generally constructed of syringe outer shell 52, inner syringe 54, plunger 56, pushing stopper 60, separation stopper 66, and injection stopper 74.

Figures 6A, 6B, 6C:
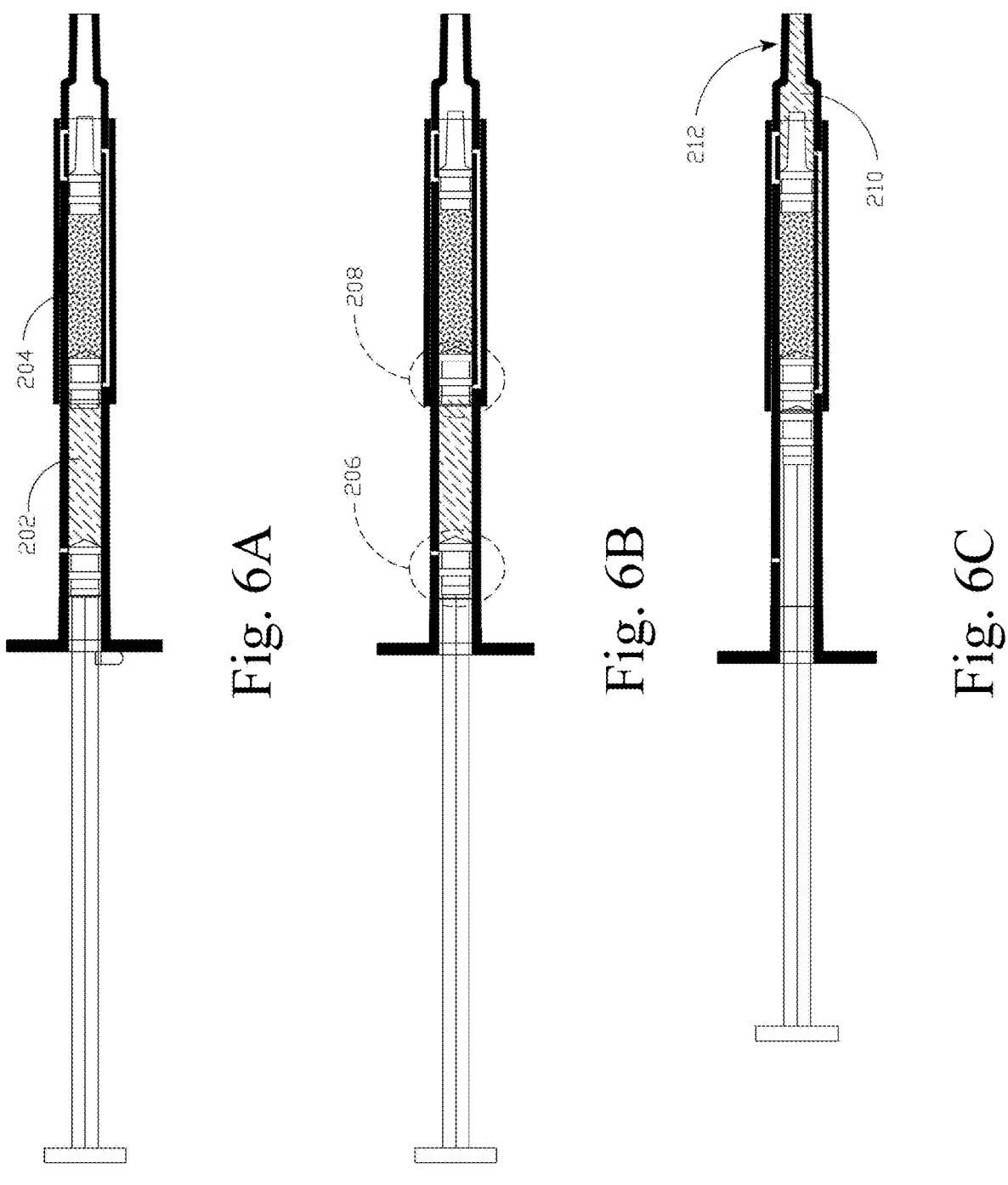
FIGS. 6A-6F are cross-sectional views of the second preferred embodiment of the delivery device of the present invention shown in progressive conditions effecting the delivery of the multiple substances.
Figures 6D, 6E, 6F:
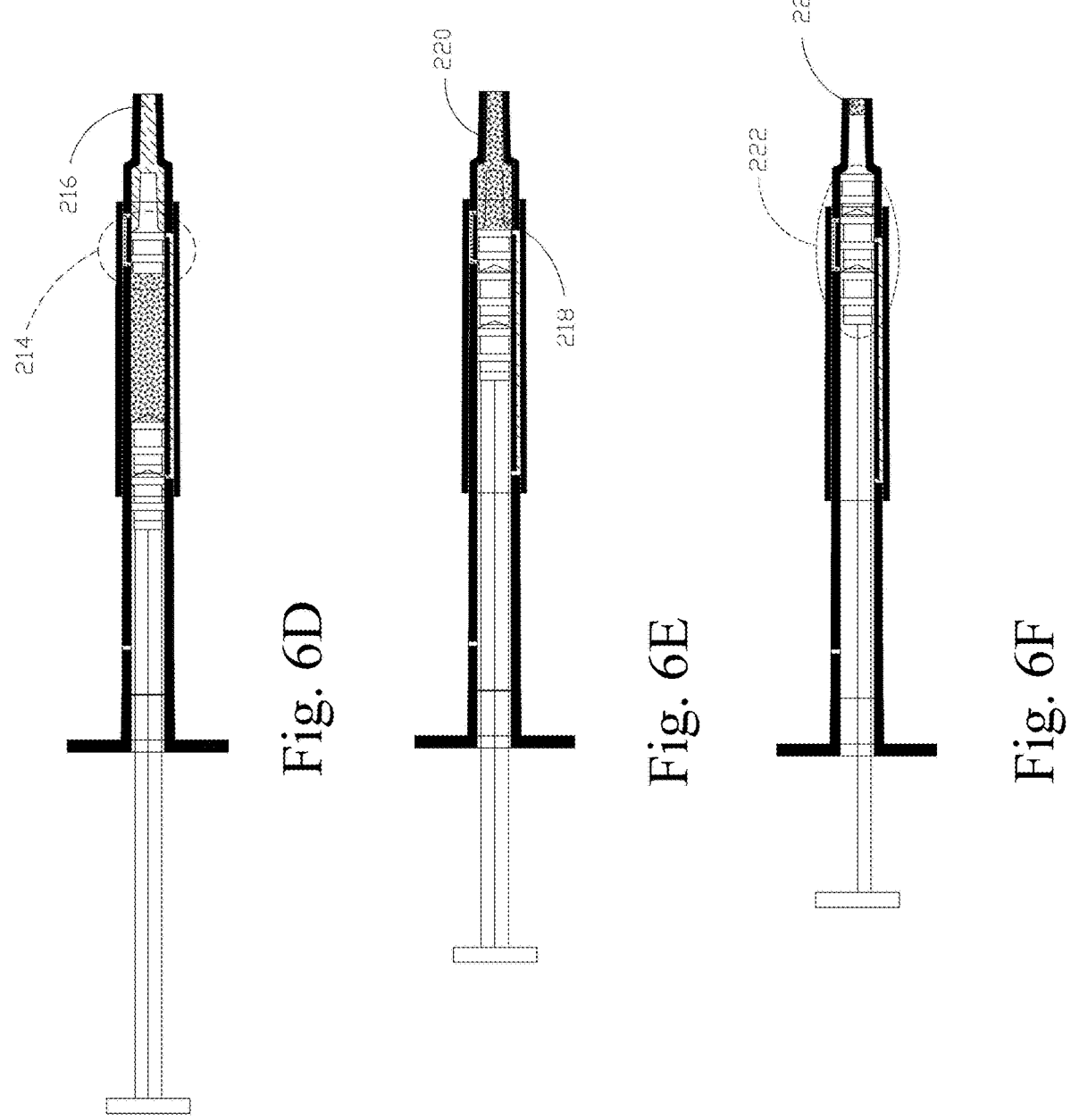

FIGS. 6A-6F are cross-sectional views of the second preferred embodiment of the delivery device of the present invention shown in progressive conditions effecting the delivery of the multiple substances. FIG. 6A shows the starting position of the device pre-filled with a first liquid at position 202 and a second liquid at position 204. FIG. 6B shows the tab removed with all stoppers advanced at positions 206 & 208 to open the first liquid bypass channel. While the separation and injection stoppers remain static, FIG. 6C shows the first liquid transferred past the second liquid at position 210 and the first liquid bypass channel closed by virtue of stopper-to-stopper contact. In the process, a significant portion of the first liquid is delivered through the nozzle at position 212. FIG. 6D shows all stoppers advanced to open the second liquid bypass channel in condition 214 while the first liquid bypass channel remains closed. FIG. 6D also shows the residual first liquid in the nozzle at position 216. FIG. 6E shows the second liquid transferred past the injection stopper at position 218 which remains static. FIG. 6E also shows the second liquid bypass channel closed with the second liquid having been moved into the nozzle at position 220. Finally, FIG. 6F shows the stoppers advanced to their final position 222 with the maximum volume of both liquids injected/dispensed by the long-tipped injection stopper at position 224.

Further Description of the Preferred Embodiments

The present invention may generally be described as a device for sequentially or concurrently dispensing, and in some embodiments mixing, two different liquids, gels, suspensions, powdered solids, etc. from a syringe. Since the syringe is to be held in the vertical (or near vertical) position by the user at the time of transfer, and/or purging of the nozzle and attached dispenser, the terms "upper" and "lower" are used with this orientation in mind (even though the appended drawings will typically show the syringe in the horizontal position). The "upper" portion of the syringe may also be identified as the "distal" end (also the "discharge" end) and the "lower" portion of the syringe may be identified as the "proximal" end (also the "stopper" end). It is intended that all but the stoppers will be formed by plastic injection molding.

First Embodiment (FIGS. 1-3)—Components & Nomenclature

Outer Cylinder 12 (Shell)

The outer cylinder or shell is designed to accept a machine fit of the inner cylinder (the inside diameter of the outer cylinder will be equal to the outside diameter of the inner cylinder), and this arrangement forms the main body of the syringe.

Inner Cylinder 14 (Syringe)

The inner surfaces of the inner cylinder or syringe form the lower and upper chambers into which the substances to be delivered will be stored until time for diluent transfer (from the lower to upper chamber) and then subsequent delivery of the mixed solution through the nozzle at the upper or distal extent of the assembled device. An integral finger grip flange is included at one end of the cylinder (the lower or proximal end in the above referenced vertical orientation).

The inner cylinder may preferably have a drilled/pierced vent hole for the purpose of allowing gas to escape as the lower stopper is inserted into the syringe with the liquid diluent in place. Once the lower stopper arrives at and covers the vent hole, the incompressible diluent will then completely fill the lower chamber such that any further insertion of the lower stopper will result in a corresponding movement of the upper stopper. The end of the inner cylinder is formed with a nozzle which is a simple tapered cylinder with a small thru hole. The outside diameter of the nozzle will be selected to exactly fit the inside diameter of the mating flange of whichever applicator device might be chosen.

Approximately midway along the length of the inner cylinder, multiple linear shallow channels are etched or molded, preferably either four at 90 degrees apart radially or two at 180 degrees apart radially, into the cylinder's outer surface. Small holes connect the ends of these channels to the inside surface and inner volume of the inner cylinder. At its initial position, the upper stopper will cover and seal off the lower (proximal) holes connecting the inside and outside surfaces of the inner cylinder thus prohibiting any flow of the lower chamber contents into the upper chamber until such time as the upper stopper moves slightly forward. The machine-fit interface between the outer and inner cylinders will maintain an effective seal so that no diluent or its subsequent solution will be able to escape in any direction. Alternately, the assembly process may utilize RF welding, glue, or other sealing methods at the upper and lower extents of the outer shell. Simply sealing the ends of the outer shells with any of these methods is more than sufficient to maintain the integrity of the inner cylinder/outer cylinder combination.

Plunger 16

The plunger is simply a push rod used to force the lower and upper stoppers, the diluent and the subsequent solution forward toward the nozzle end of the syringe. Two removable tabs limit forward motion of the plunger until such time as they are removed one at a time. The first or upper tab will stop forward motion of the lower stopper at precisely the 100% diluent fill point. Any motion beyond that point will result in the opening of the chamber-connecting channels.

As such, the upper (distal) tab will be left in place from filling and assembly until diluent transfer is about to be initiated.

The lower (proximal) removable tab will be positioned at precisely the point where the lower stopper will have completely evacuated the lower chamber and come into close contact with the lower or back surface of the upper stopper. This second tab will remain in place on the plunger and will prohibit further motion of the stoppers until such time as delivery of the solution is called for.

Lower Stopper 20 (Diluent Stopper)

The lower stopper or diluent stopper will be made of a synthetic rubber or similar material that will provide a seal against the inner walls of the lower cylinder but will be movable with appropriate force applied to the plunger. Unlike the upper stopper, the lower stopper will be approximately flat on both ends (with the exception of an appropriate mating hole to be included in the lower surface for attachment of the plunger).

Upper Stopper 28 (Injection Stopper)

The upper stopper or injection stopper will be made of the same material as that used for the lower stopper, and its lower half will contain the same profile. The upper surface, on the other hand, will be cone shaped and will exactly match the inner cone shape of the inner cylinder nozzle. This feature will allow near complete evacuation of the delivered solution after mixing.

First Embodiment Syringe (LYO)—Assembly & Filling

The syringe parts will preferably be assembled in an automated assembly line process in the following order:

(a) The inner cylinder is pressed into the outer cylinder until the outer cylinder reaches the precise location that provides complete coverage of the bypass channels and their associated holes into the inner chambers.

(b) The upper stopper is inserted to the exact depth that just seals off the inner cylinder's lower channel holes.

(c) With the partially assembled parts in a vertical orientation and the outer cylinder flange oriented up (flipped from the above-described orientation), the lower chamber is partially filled with diluent.

(d) The plunger is assembled with the lower stopper.

(e) The lower stopper with plunger attached is inserted into the open end of the inner cylinder and pressed inward (distally) until the first locking tab just touches the finger grip flange.

(f) The assembly is reoriented to vertical (flipped) with the open end of the inner cylinder oriented upward.

(g) The upper chamber is filled with the material to later be mixed with diluent.

(h) A moisture/contaminant barrier seal is applied to the nozzle's outflow end.

(i) The assembled syringe is packaged and shipped.

First Embodiment Syringe (LYO)—Application & Use (See FIGS. 3A-3E)

(a) The syringe assembly is unwrapped and the moisture/containment barrier seal is removed.

(b) The chosen applicator is inserted onto the nozzle end with a slip lock fit or half twist.

(c) The first locking tab is removed from the plunger.

(d) The syringe assembly is oriented vertically with the nozzle/applicator end up and the plunger is slowly pressed upward.

(e) The forward motion of the pressed plunger stops when the second tab comes into contact with the finger flange.

(f) The syringe is shaken or vibrated as directed by the maker of the syringe contents to assure complete mixing.

(g) When the user is ready to deliver the solution, the plunger's second tab is removed.

(h) With the syringe oriented vertically (cap/nozzle end up) the end of the plunger is gently pressed until solution begins to emerge from the end of the applicator. This will assure that no residual gas remains in the syringe or its applicator.

(i) The solution is delivered as appropriate.

(j) On completion, the entire syringe is discarded. It is not intended to be refilled or reused.

Second Embodiment (FIGS. 4-6)—Components & Nomenclature

Outer Cylinder 52 (Shell)

As with the first embodiment, the outer cylinder or shell is designed to accept a machine fit of the inner cylinder (the inside diameter of the outer cylinder will be equal to the outside diameter of the inner cylinder), and this arrangement forms the main body of the syringe.

Inner Cylinder 54 (Syringe)

The inner surfaces of the inner cylinder or syringe form the various chambers into which the substances to be mixed and delivered will be stored until time for the transfer, mixing, and subsequent delivery of the mixed solution through the nozzle at the upper or distal extent of the assembled device. An integral finger grip flange is included at one end of the cylinder (the lower or proximal end in the above referenced vertical orientation).

The inner cylinder may preferably have a drilled/pierced vent hole for the purpose of allowing gas to escape as the pushing stopper is inserted into the syringe with the first liquid in place. Once the pushing stopper arrives at and covers the vent hole, the incompressible first liquid will then completely fill the first chamber such that any further insertion of the pushing stopper will result in a corresponding movement of the separation stopper. The end of the inner cylinder is formed with a nozzle which is a simple tapered cylinder with a small thru hole. The outside diameter of the nozzle will be selected to exactly fit the inside diameter of the mating flange of whichever applicator device might be chosen.

Along part of the length of the inner cylinder, multiple linear shallow channels are etched or molded, preferably either four at 90 degrees apart radially or two at 180 degrees apart radially, into the cylinder's outer surface. Once again, in the case of the second embodiment, there are two sets/types of channels, first liquid bypass channels and second liquid bypass channels. Various radial placements of these two sets/types of channels are anticipated. Small holes connect the ends of these channels to the inside surface and inner volume of the inner cylinder. At their various initial and subsequent positions, the stoppers will cover and seal off the appropriate holes connecting the inside and outside surfaces of the inner cylinder thus prohibiting any flow of the respective lower chamber contents into the upper chambers until such time as the separation stopper moves forward and/or the injection stopper moves forward. The machine-fit interface between the outer and inner cylinders will maintain an effective seal so that no liquid or subsequent mixture will be able to escape in any direction. As mentioned above with respect to the first embodiment, the assembly process with the second embodiment may utilize RF welding, glue, or other sealing methods at the upper and lower extents of the outer shell. Simply sealing the ends of the outer shells with any of these methods is more than sufficient to maintain the integrity of the inner cylinder/outer cylinder combination.

Plunger 56

The plunger is simply a push rod used to force the various stoppers, liquids, and the subsequent mixtures forward toward the nozzle end of the syringe. One removable tab limits forward motion of the plunger until such time as it is removed. The tab will stop forward motion of the pushing stopper at precisely the first liquid fill point. Any motion beyond that point will result in the opening of the chamber-connecting channels. As such, the tab will be left in place from filling and assembly until the process of fluid transfer and mixing is about to be initiated.

Lower Stopper 60 (Pushing Stopper)

The lower stopper or pushing stopper will be made of a synthetic rubber or similar material that will provide a seal against the inner walls of the lower cylinder but will be movable with appropriate force applied to the plunger. Unlike the upper (injection) stopper, the lower (pushing) stopper will be approximately flat on both ends (with the exception of an appropriate mating hole to be included in the lower surface for attachment of the plunger).

Intermediate Stopper 66 (Separation Stopper)

The intermediate stopper or separation stopper will be made of the same material as that used for the lower (pushing) stopper and will have the same general profile. The profile of the lower surface will be generally configured to inversely match and receive the upper surface of the pushing stopper. The upper surface of the intermediate stopper will be generally the same as the upper surface of the pushing stopper.

Upper Stopper 74 (Injection Stopper)

The upper stopper or injection stopper will be made of the same material as that used for the intermediate (separation) stopper, and its lower half will contain the same profile. The upper surface, on the other hand, will be cone shaped and will exactly match the inner cone shape of the inner cylinder. This feature will allow near complete evacuation of the delivered solution through the nozzle.

Second Embodiment Syringe (DUO)—Assembly & Filling

The syringe parts will preferably be assembled in an automated assembly line process in the following order:

(a) The inner cylinder (syringe) is pressed into the outer cylinder (shell) until the outer cylinder reaches the precise location that provides complete coverage of the bypass channels and their associated holes into the inner chambers.

(b) The device is turned nozzle end down.

(c) The injection stopper is inserted well short of its final-assembly position. The initial liquid to be loaded into the device (the "second liquid" to be ultimately delivered) is filled above/behind the injection stopper until it reaches the upper opening of the first liquid bypass channel.

(d) The separation stopper is inserted until it reaches the starting position shown in the attached figures. This will force the injection stopper to travel to its starting position (with the beginning of the second liquid bypass channel closed off).

(e) The subsequent liquid to be loaded into the device (the "first liquid" to be ultimately delivered) is filled to the edge of the vent hole.

(f) With the plunger snapped into the open end of the pushing stopper, that stopper is inserted until it just seals off the vent hole (at which point, the removable tab will just come into contact with the syringe).

(g) The assembled syringe is packaged and shipped.

Second Embodiment Syringe (DUO)—Application & Use (See FIGS. 6A-6E)

(a) The syringe assembly is unwrapped.

(b) The chosen applicator is inserted onto the nozzle end with a slip lock fit or half twist.

(c) The locking tab is removed from the plunger.

(d) With the nozzle end held upright, the user begins to press the plunger upward into the device until liquid begins to escape from the nozzle (or needle if one is in use). At this point the separation stopper has moved into the bypass position and the first liquid is bypassing the second liquid chamber and begun to exit the device. The injection stopper and the separation stopper are keeping the second liquid completely contained.

(e) Injection of first liquid can begin.

(f) The pushing stopper contacts the back of the separation stopper thus positioning both to push the second liquid forward. The second liquid then forces the injection stopper forward just enough to open the second much shorter bypass channels.

(g) Continued insertion of the push plunger will then cause the second liquid to be squeezed out of its containment chamber and past the injection stopper toward the nozzle exit.

(h) At the end of the injection stroke, the long-tipped injection stopper will force the remainder of the second liquid out of the syringe leaving to waste only the small amount of liquid remaining in the needle (if used).

(i) On completion, the entire syringe is discarded. It is not intended to be refilled or reused.

General Characteristics of All Embodiments

Off-the-shelf syringes may be used for the inner cylinder application and can be slightly modified by etching shallow channels into the outside surface and by piercing/drilling tiny through holes at the ends of these channels. Stoppers normally used in these same syringes may also be used in the device. This assures proper fit and seal. For example, standard plastic 1 milliliter syringes may be used since many current vaccines use a dose of 0.3 milliliter. The device of the present invention can be viewed as a special purpose "syringe adapter" since it fits and seals over an existing syringe geometry.

For ease of manufacturing, stock plastic syringes are slightly tapered end to end so that the parts can be easily and quickly extracted from their molds. Likewise, if the tapers of mating parts are created at the same taper angle, total surface contact (and seal) can be assured even if diameter tolerances are slightly off.

A vent hole may be included in the preferred embodiments. In any case, the vent hole exists to allow air/gas to escape the syringe as the pushing stopper is inserted to the level beginning the filled liquid. The vent hole may be sealed off by the stopper as soon as the first sealing surface of the stopper passes the hole. An alternative to this approach would be the use of a small diameter wire past which the pushing stopper travels as it is inserted to the liquid level. That wire would then be extracted to finalize the sealing function of the stopper.

The second preferred embodiment described above is intended to allow the injection of two separate liquids through the same nozzle/needle exit. Three stoppers instead of two are included, and the first bypass channel allows the first liquid to completely bypass the second liquid chamber before the second and final bypass is initiated. This second embodiment finds particular use with medicines/vaccines that need to remain completely separate from each other until the moment of injection. This device will allow both liquids to be administered with a single "plunger" and without any mixing of the two until time of use. Both devices are meant to be single use and disposable, and both are to be delivered to end users pre-filled and sealed in sterile packaging.

Although the present invention has been described in terms of the foregoing preferred embodiments, this description has been provided by way of explanation only and is not intended to be construed as a limitation of the invention. Those skilled in the art will recognize modifications of the present invention that might accommodate specific liquids, gels, suspensions, powders, etc., and specific applicators. Those skilled in the art will further recognize additional methods for modifying the construction of the dispensing container/cartridges to accommodate variations in fluid viscosities, fluid quantities, dynamic pressures, spray velocities, and flow rates. Such modifications, as to structure, orientation, geometry, and even construction, where such modifications are coincidental to the types of applications involved, do not necessarily depart from the spirit and scope of the invention.

We claim:

1. A dual chamber syringe device for storing, mixing, and dispensing multiple compounds from one device, the dual chamber syringe device comprising:

a syringe outer shell, the syringe outer shell comprising a generally cylindrical wall having an interior surface with an internal diameter;

an inner syringe body, the inner syringe body comprising a generally cylindrical tube having a cylindrical wall and an exterior surface with an external diameter, the external diameter of the inner syringe body approximately equal to the internal diameter of the syringe outer shell, the exterior surface of the inner syringe body having a longitudinal channel formed therein, partially into the wall of the tube, the longitudinal channel terminating with end apertures that pass fully through the wall of the tube, the longitudinal channel with end apertures fully covered by the syringe outer shell;

a longitudinal plunger fixed with a diluent stopper on a distal end thereof, the longitudinal plunger and the diluent stopper slidingly positioned within the inner syringe body; and a floating injection stopper slidingly positioned within the inner syringe body distal of the longitudinal plunger and the diluent stopper.

\*   \*   \*   \*   \*